(12) United States Patent
Barr et al.

(10) Patent No.: US 8,563,318 B2
(45) Date of Patent: Oct. 22, 2013

(54) METHOD FOR THE DIAGNOSIS OF NON-ALCOHOLIC STEATOHEPATITIS BASED ON A METABOLOMIC PROFILE

(75) Inventors: Jonathan Barr, Derio (ES); Azucena Castro Espido, Derio (ES); Jose Maria Mato De La Paz, Derio (ES); Maria Luz Martinez Chantar, Derio (ES)

(73) Assignee: One Way Liver Genomics, S.L., Cerio-Viecaya (ES)

( * ) Notice: Subject to any disclaimer, the term of this patent is extended or adjusted under 35 U.S.C. 154(b) by 91 days.

(21) Appl. No.: 13/058,657

(22) PCT Filed: Aug. 11, 2009

(86) PCT No.: PCT/EP2009/060374
§ 371 (c)(1),
(2), (4) Date: Apr. 1, 2011

(87) PCT Pub. No.: WO2010/018165
PCT Pub. Date: Feb. 18, 2010

(65) Prior Publication Data
US 2011/0180703 A1    Jul. 28, 2011

(30) Foreign Application Priority Data
Aug. 11, 2008  (EP) .................................. 08380249

(51) Int. Cl.
*G01N 33/48* (2006.01)
*G01N 30/02* (2006.01)
*H01J 49/26* (2006.01)

(52) U.S. Cl.
USPC .............. 436/63; 436/161; 436/173; 250/282

(58) Field of Classification Search
USPC .............. 436/63, 71, 86, 161, 173; 435/4, 29; 250/281, 282
See application file for complete search history.

(56) References Cited

U.S. PATENT DOCUMENTS

| | | | |
|---|---|---|---|
| 2006/0135420 A1* | 6/2006 | Mato De La Paz et al. | .... 514/12 |
| 2006/0172286 A1 | 8/2006 | Poynard | |
| 2006/0205023 A1 | 9/2006 | Paz | |
| 2007/0037287 A1* | 2/2007 | Takatsuki et al. | ............. 436/132 |
| 2007/0231811 A1* | 10/2007 | Mato De La Paz | ................ 435/6 |
| 2009/0304704 A1* | 12/2009 | Gerhard et al. | ............ 424/141.1 |
| 2010/0068746 A1* | 3/2010 | Nakajima et al. | ............... 435/25 |
| 2011/0212468 A1* | 9/2011 | Kohli et al. | .................. 435/7.21 |
| 2012/0187289 A1* | 7/2012 | Barr et al. | ...................... 250/282 |

FOREIGN PATENT DOCUMENTS

| | | |
|---|---|---|
| EP | 1582873 A1 | 10/2005 |
| EP | 1619257 A1 | 1/2006 |
| WO | 2006082522 A1 | 8/2006 |
| WO | 2006117945 A1 | 11/2006 |
| WO | 2007136822 A2 | 11/2007 |
| WO | 2008021192 A2 | 2/2008 |
| WO | 2008041128 A2 | 4/2008 |
| WO | 2008060841 A2 | 5/2008 |

OTHER PUBLICATIONS

Kalhan et al. Abstract from FASEB Journal, vol. 22, Apr. 2008.*
Bhattacharyya et al. Abstract No. 59 from Gastroenterology, vol. 134, No. 4, supplement 1, Apr. 2008, pp. A753.*
Lelliott, C.J., et al., "Transcript and metabolite analysis of the effects of tamoxifen in rat liver reveals inhibition of fatty acid synthesis..", The FASEB Journal, 2005, pp. 1108-1119, vol. 19.
Barr, J., et al., "Liquid Chromatography—Mass Spectrometry-Based Parallel Metabolic Profiling of Human and Mouse Model Serum Reveals . . . ", "Journal of Proteome Research", 2010, pp. 4501-4512, vol. 9.

* cited by examiner

*Primary Examiner* — Maureen Wallenhorst
(74) *Attorney, Agent, or Firm* — Hultquist, PLLC; Steven J. Hultquist (57) ABSTRACT

The invention relates to methods for the diagnosis of non-alcoholic steatosis (NASH). The method relies on the determination of certain metabolic markers in a biological sample of the patient which are up- or down-regulated in the NASH patients vs. patients with a simple fatty liver (steatosis).

3 Claims, 2 Drawing Sheets

METHOD FOR THE DIAGNOSIS OF NON-ALCOHOLIC STEATOHEPATITIS BASED ON A METABOLOMIC PROFILE

CROSS-REFERENCE TO RELATED APPLICATIONS

This is a U.S. national phase under the provisions of 35 U.S.C. §371 of International Patent Application No. PCT/EP09/60374 filed Aug. 11, 2009, which in turn claims priority under 35 U.S.C. §119 of European Patent Application No. EP08380249.6 filed Aug. 11, 2008. The disclosures of such international patent application and European priority patent application are hereby incorporated herein by reference in their respective entireties, for all purposes.

FIELD OF THE INVENTION

The invention relates to the field of diagnostic methods and, more in particular, to a method for the diagnosis of non-alcoholic steatohepatitis (NASH) based on the determination of the levels of a series of metabolic markers which are altered in NASH patients with respect to patients with simple fatty liver (steatosis).

BACKGROUND OF THE INVENTION

Non alcoholic fatty liver disease (NAFLD) encompasses a wide range of conditions characterised by the build-up of fat in the liver cells of people who do not drink alcohol excessively. At one end of the scale is the relatively harmless simple fatty liver, or steatosis, that does not cause significant liver damage. If left unattended this condition may progress to more advanced conditions, some of which may be life threatening. Non-alchoholic steatohepatitis (NASH) is a significant development in NAFLD, corresponding to an aggressive condition characterised by swelling and tenderness in the liver. With intense, on-going inflammation a build up of scar tissue (fibrosis) may form, eventually leading to cirrhosis where irregular bumps, known as nodules, replace the smooth liver tissue and the liver becomes harder. The effect of this, together with continued scarring from fibrosis, means that the liver will run out of healthy cells to support normal functions. This can lead to complete liver failure. Most people with a fatty liver are overweight or obese. As more and more people lead inactive lives and carry extra weight around with them, so the number of cases of fatty liver, in particular NASH, is rising. Therefore, there is a need for diagnostic tests that may provide a robust assessment of the presence of NASH or steatosis in a patient.

There is currently no specific laboratory test for NASH, making it extremely difficult to diagnose since even people who go on to develop fibrosis and cirrhosis may undergo liver damage for many years before symptoms become apparent.

The only widely accepted test for distinguishing NASH from other forms of disease is a liver biopsy. This process involves passing a fine hollow needle through the skin and into the liver, withdrawing a small tissue of sample that is submitted for histological examination. Apart from the obvious discomfort induced by this invasive procedure, assessment is often subjective and prone to sampling error.

Several methods for the detection of NAFLD have been described to date based on measuring physico-chemical properties. For instance, scanning the liver with imaging equipment such as magnetic resonance imaging (MRI) allows the detection of fat deposits (steatosis) in the liver. WO08041128 describes a method for the diagnosis of NASH based on the determination of the electrical impedance of the liver using a pair of electrodes that are placed in contact with the liver using an open abdominal surgical procedure (laparotomy). However, this method requires direct contact of the electrodes with the liver, which makes it more appropriate for the detection of NASH in explanted livers before they are transplanted into a receptor, and does not allow the distinction between the different stages of NAFLD.

Other methods are based on the presence of different polymorphisms in genes involved in lipid metabolism. These polymorphisms may be detected in body fluids and, thus, they can be considered as non- or minimally-invasive methods. For instance, WO06117945 describes a method for the diagnosis of NASH by detecting the T94A genetic polymorphism in FABP1 in a biological sample taken from a subject.

Other methods are based on the determination of the expression levels of one or more proteins or metabolites in body fluids. In particular, WO06082522 describes a method for detecting steatosis in a patient by the determination of the levels of ApoA1, $\alpha$2-macroglobulin, alanine aminotransferase, gammaglutamyl transpeptidase and triglycerides.

WO08021192 describes a non-invasive method for the diagnosis and monitoring of liver diseases such as NASH and steatosis based on determining the levels of fatty acids and eicosanoids in a body fluid of the patient. However, this method is limited to the identification of lipid species and requires complex fractionation steps of the body fluids before the metabolites can be detected.

Lelliot et al (FASEB J., 2005, 19:1108-1119) describe a method for detecting tamoxifen-induced NASH based on the determination of metabolic profiles in blood using [$^1$H]-NMR. However, this method is performed in samples obtained by liver biopsy and thus, it is a highly invasive method.

WO07136822 describes a method for the detection of NASH from other NAFLD by determining the phosphorylation state of one or more members of the AKT/mTOR/IRS pathway in adipose tissue from a subject. However, this method requires the extraction of an adipose tissue sample from a patient, thus resulting in a minimally invasive method.

Clearly there is a need for alternative non-invasive methods to existing diagnosis methods, reducing patient discomfort and hospital-stay costs whilst providing a more robust, standardised assessment.

SUMMARY OF THE INVENTION

In a first aspect, the invention relates to a method for the differential diagnosis of the type of NAFLD in a patient comprising determining in a biological sample of said patient the level(s) of one or more of the metabolic markers defined in tables 2 and 3 and comparing the levels of said markers with the levels of the same markers in a NASH-positive sample and/or in a steatosis-positive sample wherein (i) the patient is diagnosed as having NASH when the levels of one or more of the metabolic marker or markers defined in table 2 are increased with respect to the level of the same metabolic markers in a steatosis-positive sample and/or when the levels of one or more of the metabolic marker or markers defined in table 3 are decreased with respect to the level of the same metabolic markers in a steatosis-positive sample and/or (ii) the patient is diagnosed as having steatosis when the levels of one or more of the metabolic marker or markers defined in table 2 are decreased with respect to the level of the same metabolic markers in a NASH-positive sample and/or when the levels of one or more of the metabolic marker or markers defined in table 3 are increased with respect to the level of the same metabolic markers in a NASH-positive sample.

In a second aspect, the invention relates to a method for the determination of the efficacy of a therapy for NASH comprising determining in a biological sample of a subject suffering from NASH and having been treated with said therapy the level(s) of one or more of the metabolic markers as defined in table 2 or table 3 wherein the therapy is considered as effective for the treatment of NASH when the levels of one or more of the metabolic marker(s) defined in table 2 is/are decreased with respect to the level of the same metabolic marker(s) in a reference sample and/or when the levels of one or more of the metabolic marker(s) defined in table 3 is/are increased with respect to the level of the same metabolic marker(s) in a reference sample.

In a third aspect, the invention relates to a method for the identification of compounds suitable for the treatment of NASH comprising determining in a biological sample of a subject suffering from NASH and having been treated with a candidate compound the level(s) of one or more of the metabolic markers as defined in table 2 or table 3 wherein the compound is considered as effective for the treatment of NASH or steatosis when the levels of one or more of the metabolic marker(s) defined in table 2 is/are decreased with respect to the level of the same metabolic marker(s) in a reference sample and/or when the levels of one or more of the metabolic marker(s) defined in table 3 is/are increased with respect to the level of the same metabolic marker(s) in a reference sample.

In a fourth aspect, the invention relates to a method for the identification of compounds capable of inducing NASH comprising determining in a biological sample of subject which has been treated with a candidate compound the level(s) of one or more of the metabolic markers as defined in table 2 or table 3 wherein the compound is considered as capable of inducing NASH when the levels of one or more of the metabolic marker(s) defined in table 2 is/are increased with respect to the level(s) of the same metabolic marker(s) in a reference sample and/or when the levels of one or more of the metabolic marker(s) defined in table 3 is/are decreased with respect to the level of the same metabolic marker(s) in a reference sample.

DETAILED DESCRIPTION OF THE INVENTION

I. Diagnosis of NASH or of a Predisposition to NASH

The authors of the present invention have taken a significant step to addressing the need for non-invasive methods for the diagnosis of NASH by performing metabolic profiling of patient serum samples as a non-invasive alternative for NASH diagnosis. The authors of the present invention have identified a series of metabolic markers present in the serum of patients suffering from NASH which are present at different levels with respect to the serum of patients with simple fatty liver (steatosis). These metabolic markers can then be used in a rapid non-invasive diagnostic method for NASH.

Thus, in a first aspect, the invention relates to a method (hereinafter "the first method of the invention") for the differential diagnosis of the type of NAFLD in a patient comprising determining in a biological sample of said patient the level(s) of one or more of the metabolic markers defined in tables 2 and 3 and comparing the levels of said markers with the levels of the same markers in a NASH-positive sample and/or in a steatosis-positive sample wherein (i) the patient is diagnosed as having NASH when the levels of one or more of the metabolic marker or markers defined in table 2 are increased with respect to the level of the same metabolic markers in a steatosis-positive sample and/or when the levels of one or more of the metabolic marker or markers defined in table 3 are decreased with respect to the level of the same metabolic markers in a steatosis-positive sample and/or (ii) the patient is diagnosed as having steatosis when the levels of one or more of the metabolic marker or markers defined in table 2 are decreased with respect to the level of the same metabolic markers in a NASH-positive sample and/or when the levels of one or more of the metabolic marker or markers defined in table 3 are increased with respect to the level of the same metabolic markers in a NASH-positive sample.

The expression "method for diagnosing" as referred to in accordance with the present invention means that the method may essentially consist of the aforementioned steps or may include further steps. However, it is to be understood that the method, in a preferred embodiment, is a method carried out in vitro, i.e. not practiced on the human or animal body. Diagnosing as used herein refers to assessing the probability according to which a subject is suffering from a disease. As will be understood by those skilled in the art, such an assessment, although preferred to be, may usually not be correct for 100% of the subjects to be diagnosed. The term, however, requires that a statistically significant portion of subjects can be identified as suffering from the disease or as having a predisposition therefore. Whether a portion is statistically significant can be determined without further ado by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. Preferred confidence intervals are at least 50%, at least 60%, at least 70%, at least 80%, at least 90% at least 95%. The p-values are, preferably, 0.2, 0.1, 0.05.

The term "NAFLD", as used herein, relates a group of conditions having in common the accumulation of fat in the hepatocytes. NAFLD ranges from simple fatty liver (steatosis), to nonalcoholic steatohepatitis (NASH), to cirrhosis (irreversible, advanced scarring of the liver). The term "NASH", as used herein, collectively refers to the state where the liver develops a hepatic disorder (e.g., inflammation, ballooning, fibrosis, cirrhosis, or cancer), or the state where the liver may induce such a pathological condition, and "NASH" is distinguished from "simple steatosis"; i.e., a condition in which fat is simply accumulated in the liver, and which does not progress to another hepatic-disorder-developing condition.

The term "metabolic marker", as used herein, refers to small molecule compounds, such as substrates for enzymes of metabolic pathways, intermediates of such pathways or the products obtained by a metabolic pathway. Metabolic pathways are well known in the art and may vary between species. Preferably, said pathways include at least citric acid cycle, respiratory chain, photosynthesis, photorespiration, glycolysis, gluconeogenesis, hexose monophosphate pathway, oxidative pentose phosphate pathway, production and β-oxidation of fatty acids, urea cycle, amino acid biosynthesis pathways, protein degradation pathways such as proteasomal degradation, amino acid degrading pathways, biosynthesis or degradation of: lipids, polyketides (including e.g. flavonoids and isoflavonoids), isoprenoids (including e.g. terpenes, sterols, steroids, carotenoids, xanthophylls), carbohydrates, phenylpropanoids and derivatives, alcaloids, benzenoids, indoles, indole-sulfur compounds, porphyrines, anthocyans, hormones, vitamins, cofactors such as prosthetic groups or electron carriers, lignin, glucosinolates, purines, pyrimidines, nucleosides, nucleotides and related molecules such as tRNAs, microRNAs (miRNA) or mRNAs. Accordingly, small molecule compound metabolites are preferably composed of the following classes of compounds: alcohols, alkanes, alkenes, alkines, aromatic compounds, ketones, aldehydes, carboxylic acids, esters, amines, imines, amides, cyanides, amino acids, peptides, thiols, thioesters, phosphate esters, sulfate esters, thioethers, sulfoxides, ethers, or combinations or derivatives of the aforementioned compounds. The small molecules among the metabolites may be primary metabolites which are required for normal cellular function, organ function or animal growth, development or health. Moreover, small molecule metabolites further comprise secondary metabolites having essential ecological function, e.g. metabolites which allow an organism to adapt to its environment. Furthermore, metabolites are not limited to said primary and secondary metabolites and further encompass artificial small molecule compounds. Said artificial small molecule compounds are derived from exogenously provided small molecules which are administered or taken up by an organism but are not primary or secondary metabolites as defined above. For instance, artificial small molecule compounds may be metabolic products obtained from drugs by metabolic pathways of the animal. Moreover, metabolites further include peptides, oligopeptides, polypeptides, oligonucleotides and polynucleotides, such as RNA or DNA. More preferably, a metabolite has a molecular weight of 50 Da (Dalton) to 30,000 Da, most preferably less than 30,000 Da, less than 20,000 Da, less than 15,000 Da, less than 10,000 Da, less than 8,000 Da, less than 7,000 Da, less than 6,000 Da, less than 5,000, Da, less than 4,000 Da, less than 3,000 Da, less than 2,000 Da, less than 1,000 Da, less than 500 Da, less than 300 Da, less than 200 Da, less than 100 Da. Preferably, a metabolite has, however, a molecular weight of at least 50 Da. Most preferably, a metabolite in accordance with the present invention has a molecular weight of 50 Da up to 1,500 Da. In preferred embodiments, the metabolic markers that can be used in the context of the present invention are those markers indicated in tables 2 and 3.

It will be understood that the method of the invention can be carried out by determining the level of a variable number of the metabolites defined in tables 2 and 3 in the biological sample of the subject under study. For example, the level(s) of one biomarker, two or more biomarkers, three or more biomarkers, four or more biomarkers, five or more biomarkers, six or more biomarkers, seven or more biomarkers, eight or more biomarkers, nine or more biomarkers, ten or more biomarkers, etc., including a combination of all of the metabolic markers identified in table 2 and/or in table 3. The determination of levels of combinations of the biomarkers may allow greater sensitivity and specificity in diagnosing NASH, and may allow better differentiation of NASH from other diseases that may have similar or overlapping biomarkers.

"Sample" or "biological sample" means biological material isolated from a subject. The biological sample may contain any biological material suitable for detecting the desired biomarker and may comprise cellular and/or non-cellular material from the subject. The sample can be isolated from any suitable biological tissue or fluid such as, for example, prostate tissue, blood, blood plasma, serum, urine or cerebral spinal fluid (CSF). Preferably, the samples used for the determination of the metabolite profiles are samples which can be obtained using minimally invasive procedures. In a preferred embodiment, the samples are serum samples.

The method of the invention includes the step of determining the levels of the metabolic marker or marker(s) in a sample and comparing said levels to the levels of the same markers in a reference sample wherein said reference sample is either a steatosis-positive sample or a NASH-positive sample. The terms "steatosis-positive sample" or "NASH-positive sample" relate, respectively, to samples isolated from patients which have been diagnosed with any of these conditions. Preferably, the diagnosis has been carried out by liver biopsy so that the patient is classified as suffering fatty liver or steatosis if the tissue shows fat without inflammation and damage whereas the patient is classified as having NASH when microscopic examination of the tissue shows fat along with inflammation and damage to liver cells. The steatosis-positive sample and/or the NASH-positive sample may result from the pooling of samples from one individual or a population of two or more individuals. The population, for example, may comprise three, four, five, ten, 15, 20, 30, 40, 50 or more individuals.

The levels of the metabolite or metabolites under study in the "reference sample" may be an absolute or relative amount or concentration of the biomarker, a presence or absence of the biomarker, a range of amount or concentration of the biomarker, a minimum and/or maximum amount or concentration of the biomarker, a mean amount or concentration of the biomarker, and/or a median amount or concentration of the biomarker; and, in addition, "reference levels" of combinations of biomarkers may also be ratios of absolute or relative amounts or concentrations of two or more biomarkers with respect to each other. Appropriate positive and negative reference levels of biomarkers for a particular disease state, phenotype, or lack thereof may be determined by measuring levels of desired biomarkers in one or more appropriate subjects, and such reference levels may be tailored to specific populations of subjects (e.g., a reference level may be age-matched so that comparisons may be made between biomarker levels in samples from subjects of a certain age and reference levels for a particular disease state, phenotype, or lack thereof in a certain age group). Such reference levels may also be tailored to specific techniques that are used to measure levels of biomarkers in biological samples (e.g., LC-MS, GC-MS, etc.), where the levels of biomarkers may differ based on the specific technique that is used. In a preferred embodiment, the reference sample is obtained from a healthy subject or from a subject without previous history of NAFLD.

A metabolic marker is considered to be increased in a sample from the subject under study when the levels are increased with respect to the reference sample by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%: by at least 85%, by at least 90%, by at least 95%, by at least 100%, by at least 110%, by at least 120%, by at least 130%, by at least 140% by at least 150%, or more. Similarly, the metabolic marker is considered to be decreased when its levels are decreased with respect to a reference sample by at least 5%, by at least 10%, by at least 15%, by at least 20%, by at least 25%, by at least 30%, by at least 35%, by at least 40%, by at least 45%. by at least 5094, by at least 55%. by at least 60%, by at least 65%, by at least 70%. by at least 75%, by at least 80%, by at least 85%, by at least 90%, by at least 95%, or by 100% (i.e., absent).

Moreover, the determination of the metabolites in the methods according to the present invention, comprises, preferably, a step of separation of the metabolites present in the sample prior to the analysis step. Preferably, said compound separation step yields a time resolved separation of the metabolites comprised by the sample. Suitable techniques for separation to be used preferably in accordance with the present invention, therefore, include all chromatographic separation techniques such as liquid chromatography (LC), high performance liquid chromatography (HPLC), gas chromatography (GC), thin layer chromatography, size exclusion or affinity chromatography. These techniques are well known in the art and can be applied by the person skilled in the art without further ado. Most preferably, the method of the present invention envisages the use of LC and/or GC. Suitable devices for such determination of metabolites are well known in the art. Preferably, mass spectrometry is used in particular gas chromatography mass spectrometry (GC-MS), liquid chromatography mass spectrometry (LC-MS), direct infusion mass spectrometry or Fourier transform ion-cyclotron-resonance mass spectrometry (FT-ICR-MS), capillary electrophoresis mass spectrometry (CE-MS), high-performance liquid chromatography coupled mass spectrometry (HPLC-MS), quadrupole mass spectrometry, any sequentially coupled mass spectrometry, such as MS-MS or MS-MS-MS, inductively coupled plasma mass spectrometry (ICP-MS), pyrolysis mass spectrometry (Py-MS), ion mobility mass spectrometry or time of flight mass spectrometry (TOF), of electrospray ionization mass spectrometry (ESI-MS), ESI-MSMS, ESI-MS/(MS)$^n$, matrix-assisted laser desorption ionization time-of-flight mass spectrometry (MALDI-TOF-MS), surface-enhanced laser desorption/ionization time-of-flight mass spectrometry (SELDI-TOFMS), desorption/ionization on silicon (DIOS), secondary ion mass spectrometry (SIMS), quadrupole time-of-flight (Q-TOF), atmospheric pressure chemical ionization mass spectrometry (APCI-MS), APCI-MSIMS, APCI-(MS)$^n$, atmospheric pressure photoionization mass spectrometry (APPI-MS), APPI-MSIMS, and APPI-(MS)$^n$, quadrupole mass spectrometry, Fourier transform mass spectrometry (FTMS), and ion trap mass spectrometry, where n is an integer greater than zero. Most preferably, LC-MS is used as described in detail below. Said techniques are disclosed in, e.g., Nissen, Journal of Chromatography A, 703, 1995: 37-57, U.S. Pat. No. 4,540,884 or U.S. Pat. No. 5,397,894, the disclosure content of which is hereby incorporated by reference.

In a preferred embodiment, the determination of the levels of the metabolites is carried out by mass spectrometry (MS). In a still more preferred embodiment, the biological sample is fractionated by liquid chromatography prior to the determination of the levels of the metabolic marker or markers. In a preferred embodiment, the liquid chromatography is performed on a C8 column at 40° C. The column may be eluted with a 10 minute linear gradient using a mobile phase at a flow rate of 140 µL/min, consisting of 100% solvent A (typically 0.05% formic acid) for 1 minute followed by an incremental increase of solvent B (typically acetonitrile containing 0.05% formic acid) up to 50% over a further minute, increasing to 100% B over the next 6 minutes before returning to the initial composition in readiness for the subsequent injection which proceeded a 45 s system re-cycle time.

II. Method for the Determination of the Efficacy of a Therapy for NAFLD

The invention also provides a method for the determination of the efficacy of the therapy for NASH. Thus, in another aspect, the invention relates to a method (hereinafter "the second method of the invention") for the determination of the efficacy of a therapy for NASH comprising determining in a biological sample of a subject suffering from NASH and having been treated with said therapy the level(s) of one or more of the metabolic markers as defined in table 2 or table 3 wherein the therapy is considered as effective for the treatment of NASH when the levels of one or more of the metabolic marker(s) defined in table 2 is/are decreased with respect to the level of the same metabolic marker(s) in a reference sample and/or when the levels of one or more of the metabolic marker(s) defined in table 3 is/are increased with respect to the level of the same metabolic marker(s) in a reference sample.

The different aspects of the second method of the invention (the methods used for the determination of the levels of the markers, the nature of the sample which is to be studied, the thresholds for consideration of a marker as having been increased or decreased) are essentially as defined previously in respect of the first method of the invention.

The term "reference sample", as used in respect of the second method of the invention for the determination of the efficacy of a therapy for NASH, relates to either a sample derived from the patient wherein the efficacy of the therapy is being tested but obtained from the patient prior to the administration of the therapy. In another embodiment, the reference sample is a sample from a patient suffering from NASH which has either been left untreated or which has been treated with a control therapy, preferably, the same excipient, carrier or vehicle which is used in the therapy whose efficacy for the treatment of NASH is to be assessed.

The term "therapy" as used herein, encompasses the treatment of existing NASH as well as preventative treatment (i.e., prophylaxis). Therapy includes, but is not limited to, administering an agent for treating NASH, treating associated metabolic conditions such as diabetes and hyperlipidemia, improving insulin resistance, following a balanced and healthy diet, avoiding alcohol, and avoiding unnecessary medications.

III. Method for the Identification of Compounds Suitable for the Treatment of NASH The authors of the present invention have also developed a method for the identification of a compound suitable for the treatment of NASH. The identification of a series of metabolites whose levels are increased or decreased with respect to steatosis-positive samples allows the screening for compounds in a model of NASH which are capable of restoring the levels of the markers to those found in steatosis-positive samples.

Thus, in another aspect, the invention relates to a method (hereinafter "the third method of the invention") for the identification of compounds suitable for the treatment of NASH comprising determining in a biological sample of a patient suffering from NASH and having been treated with a candidate compound the level(s) of one or more of the metabolic markers as defined in table 2 or table 3 wherein the compound is considered as effective for the treatment of NASH or steatosis when the levels of one or more of the metabolic marker(s) defined in table 2 is/are decreased with respect to the level of the same metabolic marker(s) in a reference sample and/or when the levels of one or more of the metabolic marker(s) defined in table 3 is/are increased with respect to the level of the same metabolic marker(s) in a reference sample.

The different aspects of the third method of the invention (the methods used for the determination of the levels of the markers, the nature of the sample which is to be studied, the thresholds for consideration of a marker as having been increased or decreased) are essentially as defined previously in respect of the first method of the invention.

The term "reference sample", as used in respect of the third method of the invention, relates to either a sample derived from the patient wherein the therapy is being tested but obtained from the patient prior to the administration of the therapy. In another embodiment, the reference sample is a sample from a patient suffering from NASH which has either been left untreated or which has been treated with a control therapy, preferably, the same excipient, carrier or vehicle which is used in the candidate compound which is being screened.

Examples of suitable animals for use in the screening method of the invention include, but are not limited to, mice, rats, rabbits, monkeys, guinea pigs, dogs and cats. In accordance with this embodiment, the test compound or a control compound is administered (e.g., orally, rectally or parenterally such as intraperitoneally or intravenously) to a suitable animal and the effect on the levels of one or more of the metabolites shown in tables 2 or 3 is determined. Examples of agents that can be tested according to the third method of the invention include, but are not limited to, nucleic acids (e.g., DNA and RNA), carbohydrates, lipids, proteins, peptides, peptidomimetics, small molecules and other drugs. Agents can be obtained using any of the numerous approaches in combinatorial library methods known in the art. Test compounds further include, for example, antibodies (e.g., polyclonal, monoclonal, humanized, anti-idiotypic, chimeric, and single chain antibodies as well as Fab, F(ab')2, Fab expression library fragments, and epitope-binding fragments of antibodies). Further, agents or libraries of compounds may be presented, for example, in solution, on beads, chips, bacteria, spores, plasmids or phage.

If the compound is a low-molecular weight compound, then this can be generated by various methods known to the art, preferably synthetically, in particular by combinatorial chemistry, or by biochemical methods, in particular by recombinant expression or purification from biological probes. The compound is of low molecular weight ("small molecules") or the library is composed of molecules with low molecular weight ("small molecule library"). A "small molecule" is defined as a complex collection of compounds, which are produced in a non-biological way, that means which are not produced by recombinant expression, like for instance most protein or peptide libraries. "Small molecules" can be generated by various methods known to the art, but are preferably produced by synthetically, more preferably by combinatorial chemistry, to generate a compound library with a maximum chemical diversity within the constraints of predicted attractive drug characteristics. If the compound to be assayed for its suitability for the treatment of NASH is a peptide or a peptide library, then these can be generated by various methods known to the art for their use as candidate compounds, but they are preferably produced by biochemical methods, more preferably by recombinant expression in prokaryotic or eukaryotic cells.

The compound to be tested for its suitability for the therapy of NASH can be formulated with a pharmaceutically acceptable carrier to produce a pharmaceutical composition, which can be administered to a human or other animal. A pharmaceutically-acceptable carrier can be, for example, water, sodium phosphate buffer, phosphate-buffered saline, normal saline or Ringer's solution or other physiologically-buffered saline, or other solvent or vehicle such as a glycol, glycerol, an oil such as olive oil or an injectable organic ester. A pharmaceutically acceptable carrier can also contain physiologically acceptable compounds that act, for example, to stabilize or increase the absorption of the modulatory compound. One skilled in the art would know that the choice of a pharmaceutically acceptable carrier, including a physiologically acceptable compound, depends, for example, on the route of administration of the composition.

IV. Method for the Identification of Compounds Capable of Inducing NAFLD in a Subject The identification of a profile of metabolic markers whose levels are altered in patients suffering from NASH with respect to subjects with simple fatty liver (steatosis) can be used in a method for the identification of compounds capable of inducing NASH in a subject by contacting a steatosis-positive subject with a compound suspected of causing NASH and measuring the variation in the levels of one or more of the markers indicated in tables 2 and 3.

Thus, in another aspect, the invention relates to a method (hereinafter "the fourth method of the invention") for the identification of compounds capable of inducing NASH comprising determining in a biological sample of a subject having been treated with a candidate compound the level(s) of one or more of the metabolic markers as defined in table 2 and/or table 3 wherein the compound is considered as capable of inducing NAFLD when the levels of the metabolic marker(s) defined in table 2 is/are increased with respect to the level of the same metabolic marker(s) in a reference sample and/or when the levels of the metabolic marker(s) defined in table 3 is/are decreased with respect to the level of the same metabolic marker(s) in a reference sample.

The different aspects of the fourth method of the invention (the methods used for the determination of the levels of the markers, the nature of the sample which is to be studied, the thresholds for consideration of a marker as having been increased or decreased) are essentially as defined previously in respect of the first method of the invention.

The term "reference sample", as used in respect of the fourth method of the invention, relates to either a sample derived from the subject wherein the effect of a candidate compound is tested obtained prior to the administration of the candidate compound. In another embodiment, the reference sample is a sample from a steatosis-positive subject which has either been left untreated or which has been treated with a control therapy, preferably, the same excipient, carrier or vehicle which is used in the candidate compound which is being screened.

The invention is described herein by way of the following examples which are to be construed as merely illustrative and not limitative of the invention.

EXAMPLES

Sample Collection

Sera were collected from a set of patients grouped according to the histological examination of a liver biopsy (European Standard: steatosis grade 1, 2, 3 or NASH). Sample details are displayed in Table 1.

TABLE 1

Demographic table including the features of the patients used in the present study.

| SERUM | MALE | FEMALE | WEIGHT (kg) | HEIGHT (cm) | BMI | TECHNIQUE |
|---|---|---|---|---|---|---|
| Healthy | 5 | 5 | 71 ± 6 | 169 ± 4 | 25 ± 2 | Biochemical analysis |
| Steatosis Grade 1 | 1 | 7 | 90 ± 3 | 160 ± 3 | 36 ± 1 | Biopsy |
| Steatosis Grade 2 | 2 | 5 | 99 ± 9 | 162 ± 5 | 38 ± 3 | Biopsy |
| Steatosis Grade 3 | 1 | 2 | 116 ± 15 | 164 ± 4 | 42 ± 3 | Biopsy |
| NASH | 1 | 10 | 93 ± 5 | 155 ± 2 | 39 ± 2 | Biopsy |

Metabolite Extraction

Proteins were precipitated from the serum samples (100 μl) by adding four volumes of methanol in 1.5 ml microtubes. After brief vortexing the samples were incubated overnight at −20° C. Supernatants were collected after centrifugation at 13,000 rpm for 10 minutes, dried, and resuspended in 120 μl of 80% methanol; methanol was added first, followed by a short vortex, then water, and a final vortex. The resulting extracted samples were then transferred to vials for HPLC/MS analysis. A "quality control" (QC) sample was prepared by mixing equal volumes (20 μl) from each of the samples as they were being aliquoted for analysis. This "pooled" serum was used to provide a representative "mean" sample containing all the analytes encountered during the analysis.

Chromatography

Chromatography was performed on a 1 mm i.d.×100 mm ACQUITY™ 1.7 μm C8 BEH column (Waters Corp., Milford, USA) using an ACQUITY™ HPLC system. The column was maintained at 40° C. and eluted with a 10 minute linear gradient. The mobile phase, at a flow rate of 140 μL/min, consisted of 100% solvent A (0.05% formic acid) for 1 minute followed by an incremental increase of solvent B (acetonitrile containing 0.05% formic acid) up to 50% over a further minute, increasing to 100% B over the next 6 minutes before returning to the initial composition in readiness for the subsequent injection which proceeded a 45 s system re-cycle time.

Mass Spectrometry

The eluent was introduced into the mass spectrometer (Waters LCT Premier) by electrospray ionisation, with capillary and cone voltages set in positive and negative ion modes to 3200 V and 30 V, and 2800 V and 50 V respectively. The nebulization gas was set to 500 L/h at a temperature of 200° C. The cone gas was set to 50 L/h and the source temperature set to 120° C. Centroid data were acquired from m/z 50-1000 using an accumulation time of 0.2 s per spectrum. All spectra were mass corrected in real time by reference to leucine enkephalin, infused at 50 μL/min through an independent reference electrospray, sampled every 5 s. An appropriate test mixture of standard compounds was analysed before and after the entire set of randomized, triplicated sample injections in order to examine the retention time stability, mass accuracy and sensitivity of the system throughout the course of the run which lasted a maximum of 36 h per batch of samples injected.

Data Processing

All data were processed using the MarkerLynx application manager for MassLynx 4.1 software. The LC/MS data are peak-detected and noise-reduced in both the LC and MS domains such that only true analytical peaks are further processed by the software (e.g. noise spikes are rejected). A list of intensities of the peaks detected is then generated for the first sample, using the retention time (RT) and m/z data pairs as the identifier for each peak. This process is repeated for each LC/MS run and the data from each LC/MS analysis in the batch are then sorted such that the correct peak intensity data for each RT-m/z pair are aligned in the final data table. The ion intensities for each peak detected are then normalised, within each sample, to the sum of the peak intensities in that sample. The resulting normalised peak intensities are then multiplied by 10,000 to form a single matrix with RT-m/z pairs for each file in the dataset.

Analysis of Patient Metabolic Profiles

Figure 1:
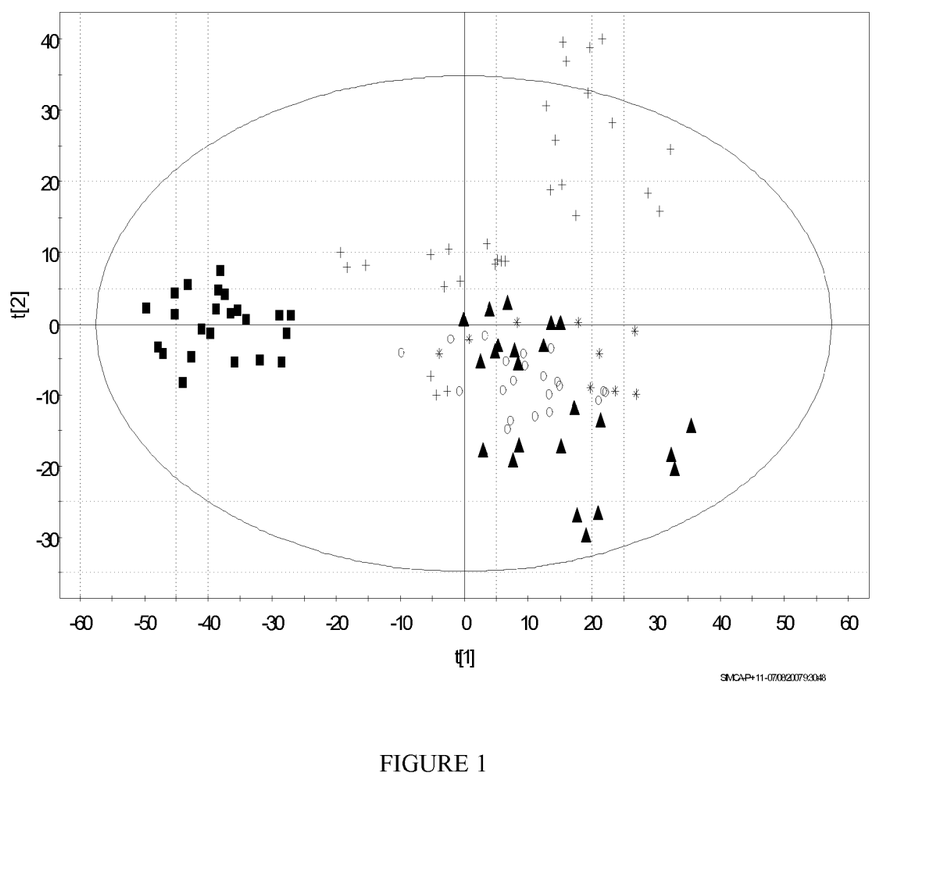
FIG. 1-PLS-DA Analysis: Healthy subjects vs. NAFLD patients. Healthy (■), Steatosis grade 1 (▲), Steatosis grade 2 (○), Steatosis grade 3 (◇), NASH (+)

Partial least-squares discriminant analysis, PLS-DA, was used to compare the metabolic profiles for samples from subjects having NAFLD to the metabolic profiles of healthy control subjects. The result of this analysis is shown in FIG. 1 where a clear separation between healthy and NAFLD patients is seen in the first component (t1). The second component (t2) explains progress through the different stages of NAFLD, where a more positive score corresponds to increasing severity—from grade 1 steatosis (−ve t2) to NASH (+ve t2).

Biomarker Discovery

Figure 2:
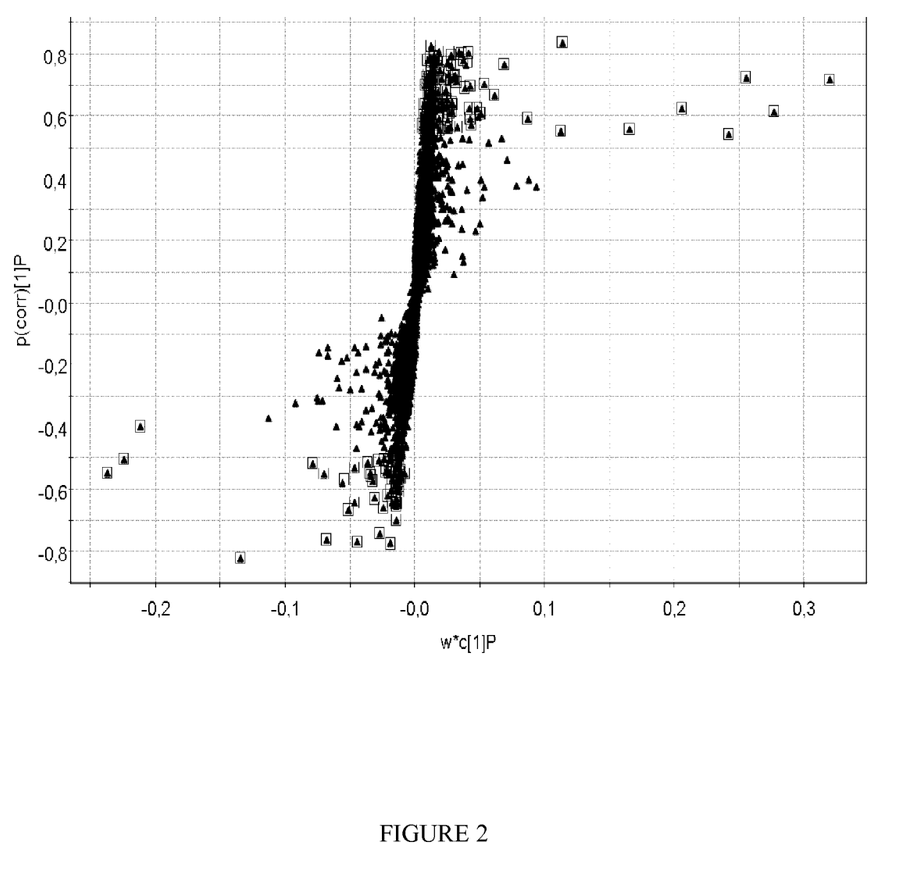
FIG. 2. OPLS Analysis: Steatosis grade 1 subjects vs. NASH subjects. Selection of candidate biomarkers (highlighted) is accomplished by filtering the corresponding loadings profile.

The orthogonal partial least-squares to latent structures (OPLS-DA) analysis procedure was used for biomarker discovery. In this approach the PLS model is rotated such that class information is found in the first predictive component, tp (correlated variation), whilst variation not related to class separation is seen in orthogonal components (uncorrelated variation). The S plot corresponding to this analysis may then be used to visualize the correlation (y-axis) between the RT-m/z pairs (corresponding to the metabolites) and the modelled class designation; the x-axis explains relative contribution of the different markers to the model. OPLS-DA analysis was carried out between steatosis grade 1 and NASH samples. FIG. 2 shows the S-plot corresponding to this analysis, revealing a number of candidate biomarkers, highlighted in red, both up- and down-regulated.

Tables 2 and 3 contain the normalised peak intensities, with associated standard errors, of a series of biomarkers for distinguishing patients with steatosis vs. patients diagnosed with NASH. Table 2 contains those markers which were up-regulated in NASH-patients with respect to patients suffering from steatosis grade 1. Table 3 contains those markers which were down-regulated in NASH-patients with respect to patients suffering from steatosis grade 1. The identities of these biomarkers are not known at this time. Such identities are not necessary for the identification of the biomarkers in subject samples, since the RT-m/z pair information shown in the table is sufficient to allow such identification.

TABLE 2

Normalized peak intensities in NAFLD-patients and steatosis grade 1 patients subjects and retention times of the metabolic markers which are up-regulated in NASH patients with respect to steatosis grade 1 patients.

| Metabolite | Rt | m/z | NASH |
|---|---|---|---|
| Metabolite_1 | 2.80 | 541.2647 | 13.7 (1.19) |
| Metabolite_2 | 3.06 | 567.3160 | 6.58 (1.09) |
| Metabolite_3 | 3.32 | 528.2631 | 53.2 (11.25) |
| Metabolite_4 | 4.67 | 450.2983 | 0.89 (0.24) |
| Metabolite_5 | 5.94 | 305.2472 | 17.03 (2.79) |
| Metabolite_6 | 6.40 | 449.3633 | 3.03 (0.81) |
| Metabolite_7 | 7.29 | 773.5780 | 20.53 (1.38) |
| Metabolite_8 | 7.60 | 775.5955 | 6.62 (0.58) |
| Metabolite_9 | 7.73 | 731.6121 | 2.81 (0.68) |
| Metabolite_10 | 7.87 | 792.5976 | 4.62 (1.1) |

| Metabolite | Steatosis grade 1 | Fold up-regulation |
|---|---|---|
| Metabolite_1 | 11.06 (1.02) | 1.239 |
| Metabolite_2 | 3.87 (0.62) | 1.700 |
| Metabolite_3 | 34.04 (4.45) | 1.563 |
| Metabolite_4 | 0.48 (0.13) | 1.854 |
| Metabolite_5 | 13.52 (1.78) | 1.260 |
| Metabolite_6 | 1.56 (0.43) | 1.942 |
| Metabolite_7 | 18.09 (0.87) | 1.135 |
| Metabolite_8 | 5.29 (0.29) | 1.251 |
| Metabolite_9 | 1.77 (0.35) | 1.588 |
| Metabolite_10 | 3.04 (0.61) | 1.520 |

TABLE 3

Normalized peak intensities in NAFLD-patients and steatosis grade 1 patients subjects and retention times of the metabolic markers which are down-regulated in NASH patients with respect to steatosis grade 1 patients.

| Metabolite | Rt | m/z | NASH |
|---|---|---|---|
| Metabolite_1 | 3.55 | 481.2801 | 2.28 (0.53) |
| Metabolite_2 | 3.98 | 526.3096 | 5.18 (1.11) |
| Metabolite_3 | 3.99 | 482.3247 | 13.92 (1.51) |
| Metabolite_4 | 6.18 | 691.5010 | 2.71 (0.72) |
| Metabolite_5 | 6.30 | 717.5174 | 11.41 (1.29) |
| Metabolite_6 | 6.31 | 673.5300 | 18.57 (2.34) |
| Metabolite_7 | 6.43 | 705.5185 | 2.27 (0.32) |
| Metabolite_8 | 6.44 | 661.5297 | 4.72 (0.6) |
| Metabolite_9 | 6.70 | 675.5440 | 83.41 (11.34) |
| Metabolite_10 | 7.19 | 778.5481 | 2.84 (0.59) |
| Metabolite_11 | 7.39 | 792.5598 | 7.64 (0.75) |
| Metabolite_12 | 7.48 | 812.5450 | 1.5 (0.21) |
| Metabolite_13 | 7.50 | 788.5443 | 4.44 (0.34) |
| Metabolite_14 | 7.51 | 744.5607 | 30.97 (2.21) |
| Metabolite_15 | 7.80 | 746.5771 | 4.46 (0.56) |
| Metabolite_16 | 7.86 | 772.5921 | 9.7 (1.65) |

| Metabolite | Steatosis Grade 1 | Fold down-regulation |
|---|---|---|
| Metabolite_1 | 4.49 (0.94) | 0.508 |
| Metabolite_2 | 6.89 (1.28) | 0.752 |
| Metabolite_3 | 17.95 (1.23) | 0.775 |
| Metabolite_4 | 4.36 (0.72) | 0.622 |
| Metabolite_5 | 16.24 (1.19) | 0.703 |
| Metabolite_6 | 24.03 (1.08) | 0.773 |
| Metabolite_7 | 3.72 (0.45) | 0.610 |
| Metabolite_8 | 6.34 (0.55) | 0.744 |
| Metabolite_9 | 106.25 (5.81) | 0.785 |
| Metabolite_10 | 5.11 (0.51) | 0.556 |
| Metabolite_11 | 10.35 (0.89) | 0.738 |
| Metabolite_12 | 2.07 (0.34) | 0.725 |
| Metabolite_13 | 5.15 (0.37) | 0.862 |
| Metabolite_14 | 36.7 (2.77) | 0.844 |
| Metabolite_15 | 6.48 (0.67) | 0.688 |
| Metabolite_16 | 12.01 (0.8) | 0.808 |

Diagnosis

The identification of biomarkers for NASH allows for the diagnosis of NASH in subjects presenting one or more symptoms of NASH. A method of diagnosing (or aiding in diagnosing) whether a subject has NASH comprises (1) analysing a serum sample from a subject to determine the level(s) of one or more biomarkers of NASH in the sample and (2) comparing the level(s) of the one or more biomarkers in the sample to NASH-positive and/or NASH-negative reference levels of the one or more biomarkers in order to diagnose (or aid in the diagnosis of) whether the subject has NASH. The one or more biomarkers that are used are selected from Tables 2 and 3. When such a method is used to aid in the diagnosis of NASH, the results of the method may be used along with other methods (or the results thereof) useful in the clinical determination of whether a subject has NASH.

The invention claimed is:

1. A method for the differential diagnosis of the type of non alcoholic fatty liver disease (NAFLD) in a patient comprising determining in a biological sample of said patient the level(s) of one or more of the metabolic markers defined in Table 2:

and Table 3:

TABLE 3-continued

Normalized peak intensities in NAFLD-patients and steatosis grade 1 patients subjects and retention times of the metabolic markers which are down-regulated in NASH patients with respect to steatosis grade 1 patients.

| | | | |
|---|---|---|---|
| Metabolite_9 | 6.70 | 675.5440 | 83.41 (11.34) |
| Metabolite_10 | 7.19 | 778.5481 | 2.84 (0.59) |
| Metabolite_11 | 7.39 | 792.5598 | 7.64 (0.75) |
| Metabolite_12 | 7.48 | 812.5450 | 1.5 (0.21) |
| Metabolite_13 | 7.50 | 788.5443 | 4.44 (0.34) |
| Metabolite_14 | 7.51 | 744.5607 | 30.97 (2.21) |
| Metabolite_15 | 7.80 | 746.5771 | 4.46 (0.56) |
| Metabolite_16 | 7.86 | 772.5921 | 9.7 (1.65) |

| Metabolite | Steatosis Grade 1 | Fold down-regulation |
|---|---|---|
| Metabolite_1 | 4.49 (0.94) | 0.508 |
| Metabolite_2 | 6.89 (1.28) | 0.752 |
| Metabolite_3 | 17.95 (1.23) | 0.775 |
| Metabolite_4 | 4.36 (0.72) | 0.622 |
| Metabolite_5 | 16.24 (1.19) | 0.703 |
| Metabolite_6 | 24.03 (1.08) | 0.773 |
| Metabolite_7 | 3.72 (0.45) | 0.610 |
| Metabolite_8 | 6.34 (0.55) | 0.744 |
| Metabolite_9 | 106.25 (5.81) | 0.785 |
| Metabolite_10 | 5.11 (0.51) | 0.556 |
| Metabolite_11 | 10.35 (0.89) | 0.738 |
| Metabolite_12 | 2.07 (0.34) | 0.725 |
| Metabolite_13 | 5.15 (0.37) | 0.862 |
| Metabolite_14 | 36.7 (2.77) | 0.844 |
| Metabolite_15 | 6.48 (0.67) | 0.688 |
| Metabolite_16 | 12.01 (0.8) | 0.808 | and comparing the levels of said markers with the levels of the same markers in a non-alcoholic steatohepatitis (NASH) positive sample and/or in a steatosis-positive sample wherein
- (i) the patient is diagnosed as having NASH when the levels of one or more of the metabolic marker or markers defined in Table 2 are increased with respect to the level of the same metabolic markers in a steatosis-positive sample and/or when the levels of one or more of the metabolic marker or markers defined in Table 3 are decreased with respect to the level of the same metabolic markers in a steatosis-positive sample and/or
- (ii) the patient is diagnosed as having steatosis when the levels of one or more of the metabolic marker or markers defined in Table 2 are decreased with respect to the level of the same metabolic markers in a NASH-positive sample and/or when the levels of one or more of the metabolic marker or markers defined in Table 3 are increased with respect to the level of the same metabolic markers in a NASH-positive sample;

wherein the determination of the level of the one or more biological markers is carried out by mass spectrometry (MS) and wherein the biological sample is fractionated by liquid chromatography prior to the determination of the levels of the metabolic marker or markers.

2. The method as defined in claim 1 wherein the biological sample is serum.

3. The method as defined in claim 1 which comprises analyzing the levels of at least two, at least three, at least four, at least five, at least ten or at least fifteen of the biomarkers selected from Tables 2 and 3.

* * * * *

UNITED STATES PATENT AND TRADEMARK OFFICE
CERTIFICATE OF CORRECTION

PATENT NO. : 8,563,318 B2  
APPLICATION NO. : 13/058657  
DATED : October 22, 2013  
INVENTOR(S) : Jonathan Barr Page 1 of 1

It is certified that error appears in the above-identified patent and that said Letters Patent is hereby corrected as shown below:

On the title page, item (73), the Assignee address
"Cerio-Viecaya (ES)"
should be
--Derio-Viecaya (ES)--

In the Specifications

At Column 11, Line 24-25,
"...transferred to vials for HPLC/MS analysis..."
should be
--...transferred to vials for UPLC/MS analysis...--

At Column 11, Line 33-34,
"using an AQUITY™ HPLC system. The column was maintained at 40° C. and eluted..."
should be
--using an AQUITY™ UPLC system. The column was maintained at 40° C and eluted...--

Signed and Sealed this
Twenty-eighth Day of January, 2014

Michelle K. Lee
*Deputy Director of the United States Patent and Trademark Office*

UNITED STATES PATENT AND TRADEMARK OFFICE
CERTIFICATE OF CORRECTION

PATENT NO.        : 8,563,318 B2
APPLICATION NO.   : 13/058657
DATED             : October 22, 2013
INVENTOR(S)       : Jonathan Barr Page 1 of 1

It is certified that error appears in the above-identified patent and that said Letters Patent is hereby corrected as shown below:

On the title page, item (73), the Assignee address
    "Cerio-Viecaya (ES)"
should be
    --Derio-Vizcaya (ES)--

In the Specifications

At Column 11, Line 24-25,
    "...transferred to vials for HPLC/MS analysis..."
should be
    --...transferred to vials for UPLC/MS analysis...--

At Column 11, Line 33-34,
    "using an AQUITY™ HPLC system. The column was maintained at 40° C. and eluted..."
should be
    --using an AQUITY™ UPLC system. The column was maintained at 40° C and eluted...--

This certificate supersedes the Certificate of Correction issued January 28, 2014.

Signed and Sealed this
Thirteenth Day of May, 2014

Michelle K. Lee
*Deputy Director of the United States Patent and Trademark Office*

UNITED STATES PATENT AND TRADEMARK OFFICE
CERTIFICATE OF CORRECTION

PATENT NO.        : 8,563,318 B2  
APPLICATION NO.   : 13/058657  
DATED             : October 22, 2013  
INVENTOR(S)       : Jonathan Barr Page 1 of 1

It is certified that error appears in the above-identified patent and that said Letters Patent is hereby corrected as shown below:

On the title page, item (73), the Assignee address
"Cerio-Viecaya (ES)"
should be
--Derio-Vizcaya (ES)--

In the Specification

At Column 11, Line 24-25,
"...transferred to vials for HPLC/MS analysis..."
should be
--...transferred to vials for UPLC/MS analysis...--

At Column 11, Line 33-34,
"using an AQUITY™ HPLC system. The column was maintained at 40° C. and eluted..."
should be
--using an AQUITY™ UPLC system. The column was maintained at 40° C and eluted...--

This certificate supersedes the Certificates of Correction issued January 28, 2014 and May 13, 2014.

Signed and Sealed this  
Fifth Day of August, 2014

Michelle K. Lee  
*Deputy Director of the United States Patent and Trademark Office*